US009317635B2

(12) United States Patent
O'Connor et al.

(10) Patent No.: US 9,317,635 B2
(45) Date of Patent: Apr. 19, 2016

(54) PROCESSES AND SYSTEMS FOR PREDICTING CORROSION

(71) Applicants: Andrew Thomas O'Connor, Lafayette, LA (US); Kyrolos Paul El Giheny, Richmond, CA (US); Sara Christine Parten, Pinole, CA (US); Benjamin Roy Crowder, London (GB); David Lawrence Cooke, San Rafael, CA (US); Eugene Vladimirovich Stepanov, Richmond, CA (US); Teppei Suzuki, Chiba (JP); Bart Quentin Welch, Mobile, AL (US)

(72) Inventors: Andrew Thomas O'Connor, Lafayette, LA (US); Kyrolos Paul El Giheny, Richmond, CA (US); Sara Christine Parten, Pinole, CA (US); Benjamin Roy Crowder, London (GB); David Lawrence Cooke, San Rafael, CA (US); Eugene Vladimirovich Stepanov, Richmond, CA (US); Teppei Suzuki, Chiba (JP); Bart Quentin Welch, Mobile, AL (US)

(73) Assignee: Chevron U.S.A. Inc., San Diego, CA (US)

( * ) Notice: Subject to any disclaimer, the term of this patent is extended or adjusted under 35 U.S.C. 154(b) by 499 days.

(21) Appl. No.: 13/929,037

(22) Filed: Jun. 27, 2013

(65) Prior Publication Data
US 2014/0005995 A1 Jan. 2, 2014

Related U.S. Application Data

(60) Provisional application No. 61/666,133, filed on Jun. 29, 2012, provisional application No. 61/666,149, filed on Jun. 29, 2012.

(51) Int. Cl.
*G06F 17/50* (2006.01)
*G01N 17/02* (2006.01)

(52) U.S. Cl.
CPC ............ *G06F 17/5009* (2013.01); *G01N 17/02* (2013.01); *G06F 2217/16* (2013.01)

(58) Field of Classification Search
USPC .......... 703/2, 12; 700/266; 166/275; 324/700
See application file for complete search history.

(56) References Cited

U.S. PATENT DOCUMENTS 3,996,124 A * 12/1976 Eaton ..................... G01N 17/02
204/404
6,282,497 B1 * 8/2001 Bharathan ................ F28B 3/02
700/266

(Continued)

FOREIGN PATENT DOCUMENTS

WO 2010-019763 2/2010

OTHER PUBLICATIONS

Quiroga, Pilar et al., *Improving Amine Unit Reliability with On-line Corrosion Monitoring & Modeling*, 2008, XP002716803 (http://www.onepetro.org/mslib/servlet/onepetropreview?id=NACE-08421 [retrieved on Nov. 22, 2013]abstract, introduction.

(Continued)

*Primary Examiner* — Thai Phan
(74) *Attorney, Agent, or Firm* — Melissa Patangia

(57) ABSTRACT

Systems and methods for evaluating the corrosion risk in operations with equipment for the handling an acid gas-containing solutes, e.g., an amine unit for the removal of acid gases such as $H_2S$, $CO_2$, etc., are provided. Input parameter values corresponding to geometrical parameters of at least an equipment (or a portion of an equipment) susceptible to corrosion risk, operating parameters, fluid dynamic properties, and properties of the solute are received by the system. Based on the input values, the systems and methods derive a minimum pressure above which acid gas flashing occurs given the localized pressure drop, causing corrosion in the identified location. In one embodiment, the systems and methods provide an assessment correlating acid gas loadings with the corrosion risk.

43 Claims, 5 Drawing Sheets

(56) References Cited

U.S. PATENT DOCUMENTS

| | | | | |
|---|---|---|---|---|
| 7,926,277 B2* | 4/2011 | Harpster | ............... | F28B 9/10 60/685 |
| 8,871,306 B2* | 10/2014 | Niccolls | ............... | C23C 28/00 427/202 |
| 2008/0116907 A1* | 5/2008 | Butler | ............... | G01N 17/00 324/700 |
| 2009/0193899 A1* | 8/2009 | Panetta | ............... | G01N 29/07 73/622 |
| 2010/0224365 A1* | 9/2010 | Abad | ............... | E21B 43/26 166/275 |
| 2010/0263195 A1* | 10/2010 | Niccolls | ............... | B32B 1/08 29/527.1 |
| 2010/0266788 A1* | 10/2010 | Niccolls | ............... | B32B 1/08 428/34.1 |

OTHER PUBLICATIONS

PCT Notificatin of Transmittal of the International Search Report and the Written Opinion o fthe International Searching Authority, or the Declaration; PCT Application No. PCT/US2013/048091; dated Dec. 3, 2013 (11 pgs).

\* cited by examiner

PROCESSES AND SYSTEMS FOR PREDICTING CORROSION

CROSS-REFERENCE TO RELATED APPLICATIONS

This application claims priority to Provisional U.S. Patent Application Nos. 61/666,133 and 61/666,149, all with a filing date of Jun. 29, 2012.

TECHNICAL FIELD

The invention relates to systems and methods for assessment of corrosion and erosion-corrosion induced by outgassing or vaporization of acid gases in liquid systems, including but not limited to amine units.

BACKGROUND

Exploration and production of deeper, lower quality oil and gas reserves has challenged refiners and gas processors with feedstocks having significantly higher sulfur content, increasing corrosion risks. Amine units for amine gas treating (also known as "gas sweetening" or "acid gas removal") refers to a group of processes or units that use aqueous solutions of various alkylamines (commonly referred to simply as amines) for the removal of $H_2S$ and $CO_2$ from gases. The removal is driven by either required product specification, e.g., natural gas that contains less than 4 ppm $H_2S$, or by environmental permission requirements.

Amine units are commonly used in refineries as well as in petrochemical plants, natural gas processing plants, and other industries. The increased level of changing ratios of $H_2S$ and $CO_2$ in the gas feedstock has significant impact on the corrosion rate and overall unit performance of amine units. Besides amine units, there are other areas with corrosion problems due to chemically absorbed gases in liquid systems. Hydroprocessing is an important process wherein sulfur and nitrogen compounds in the crude oil feed are converted to hydrogen sulfide and ammonia. As the effluent stream from the reactor cools down, the ammonia and hydrogen sulfide combine to form solid ammonium bisulfide. To reduce corrosion, wash water is introduced in the system since ammonium bisulfide is highly soluble in water, generating sour water. Corrosion in units handling the alkaline sour water containing ammonium bisulfide has been a problem for the industries for years, particularly in Reactor Effluent Air Coolers (REAC) and adjacent pipings.

Outside the oil & gas industries, in other industries such as the food and pharmaceutical industries, there are corrosion issues due to the materials being handled, e.g., chlorinated water, beer (a weak acid), etc., particularly with the vaporization of the chemically absorbed gases in the liquid being handled in the systems such as $CO_2$ and chlorine. Corrosion due to the presence and release of $SO_2$, $NO_2$, $CO_2$, etc. is an issue in steam generation operations. Plant economics are negatively impacted by the loss of revenue due to unplanned corrosion caused plant outages, shutdown to repair impacted equipment, and repair cost due to the corrosion damage.

Methods and systems have been developed to predict and/or evaluate corrosivity impact on amine units. Predict®-Amine model is a software tool that models corrosion rates in rich amine systems based on parameters including acid loadings ($H_2S$ and $CO_2$), heat stable amine salt (HSAS) concentration, flow velocity/shear stress, and operating temperature. Another model is a modified TSWEET® computer model from Bryan Research and Engineering that predicts corrosion when the $H_2S$ content in the amine solution is less than a pre-determined minimum value; or the gas phase $H_2S$ content is less than 5%.

Methods and systems in the prior art can dramatically under-predict corrosion rate. There is still a need for improved methods to evaluate corrosivity due to chemically absorbed gases in liquid systems, e.g., corrosion in amine units, taking into account the effect of acid gas flashing on localized corrosion, allowing for the optimization of plant operations.

SUMMARY

In one aspect, a method for evaluating corrosion risk in a unit for the handling of acid gas-containing solutes is disclosed. The method comprises: identifying at least a location in the unit for conducting the corrosion risk evaluation; receiving information about geometrical parameters of the location; receiving information about operating parameters, fluid dynamic properties, and properties of the liquid system; correlating fluid dynamics of the location in the unit with a shear stress value; predicting a corrosion rate for different gas loading responsive to the correlated shear stress; evaluating a localized pressure drop in the location due to the geometrical parameters; correlating a relationship between vapor saturation pressure and temperature data for the different gas loadings in the liquid system; and identifying from the correlated vapor saturation pressure and temperature data a minimum pressure above which gas flashing occurs given the localized pressure drop, causing corrosion in the identified location.

In another aspect, a method for evaluating corrosion risk in an amine unit for removing $H_2S$ acid gas is disclosed. The method comprises: identifying a plurality of locations in the amine unit to identify a maximum gas loading rate for each location; receiving information about geometrical parameters of each location; receiving information about operating parameters, fluid dynamic properties, and properties of amine in the amine unit; correlating fluid dynamics of each location in the amine unit with a shear stress value; predicting a corrosion rate for each location at different concentrations of $H_2S$ in amine as acid gas loadings responsive to the correlated shear stress for each location; evaluating localized pressure drop in each location due to the geometrical parameters; correlating a relationship between vapor saturation pressure and temperature data for the different acid gas loadings; and identifying from the correlated vapor saturation pressure and temperature data a maximum acid gas loading for each of the identified locations, given the localized pressure drop in each location, above which maximum loading rate flashing of $H_2S$ occurs.

In a third aspect, a system for evaluating corrosion risk in a unit for the handling of acid gas-containing solutes is disclosed. The system comprises a processor, which is configured to: receive information about geometrical parameters of a location within the unit; receive information about properties of the solute, fluid dynamic properties, and operating parameters in the unit; correlate fluid dynamics of the location in the unit with a shear stress value; predict a corrosion rate for different acid gas loadings responsive to the correlated shear stress; evaluate a localized pressure drop in the location due to the geometrical parameters; correlate a relationship between vapor saturation pressure and temperature data for the different acid gas loadings; and determine from the correlated vapor saturation pressure and temperature data a maximum acid gas loading, given the localized pressure drop in the location, above which maximum loading rate flashing of acid gas occurs.

In yet another aspect, a computerized prediction system for identifying locations within an amine unit susceptible to corrosion risk is disclosed. The computerized system comprises: one or more processing units for executing program instructions; and a program memory, coupled to one or more processing units, for storing a computer program including program instructions that when executed by the one or more processing units, is capable of causing the computer system to perform a number of operations. The computerized operations comprise: receiving information about geometrical parameters of at least a location in the amine unit; receiving information about operating parameters, fluid dynamic properties, and properties of amine in the amine unit; correlating fluid dynamics of the location in the amine unit with a shear stress value; predicting a corrosion rate for different acid gas loadings responsive to the correlated shear stress; evaluating a localized pressure drop in the location due to the geometrical parameters; correlating a relationship between vapor saturation pressure and temperature data for the different acid gas loadings; and identifying from the correlated vapor saturation pressure and temperature data a maximum acid gas loading, given the localized pressure drop in the location, above which maximum loading rate flashing of acid gas occurs causing corrosion in the location.

DRAWINGS

The file of this patent contains at least one drawing executed in color. Copies of this patent with color drawing(s) will be provided to the US Patent and Trademark Office upon request and payment of the necessary fee(s).

DETAILED DESCRIPTION

The following terms will be used throughout the specification and will have the following meanings unless otherwise indicated.

The term "amine" refers to amines for use in gas treating, including but not limited to monoethanolamine (MEA), diethanolamine (DEA), methyldiethanolamine (MDEA), aminoethoxyethanol(diglycoamine) (DGA), diisopropylamine (DIPA), proprietary amines known in the art and commercially available, and mixtures thereof. The most commonly used amines are the alkanolamines such as MEA, DEA, and MDEA.

The term "acid gas" refers to a gas in a liquid, and upon release (e.g., flashing) causing corrosion, e.g., $H_2S$, $CO_2$, $SO_2$ and $SO_2$ ($SO_x$), NO and $NO_2$ ($NO_2$), chlorine, etc. In one embodiment, the acid gas is chemically absorbed in the liquid (solution or fluid). In another embodiment, the acid gas is dissolved in the liquid.

The term "acid-gas containing solute" (or solution or fluid) or "solute that contains acid gas" refers to a solution, e.g., amine solution, sour water, etc., having a concentration of acid gas within (e.g., dissolved or chemically absorbed). The acid gas upon release can cause corrosion to equipment in the operations.

In the sections that follow, the reference to "amine" is by way of exemplification only for a solute in which an acid gas is chemically absorbed and can be subsequently released causing corrosion. Similarly, the reference to "$H_2S$" is by way of exemplification only for an acid gas that can be chemically absorbed in a liquid system, e.g., amine, sour water, and can be subsequently released causing corrosion, and does not exclude other acid gases or mixtures thereof, e.g., mixture of $H_2S$ and $CO_2$, mixture of $SO_2$, $NO_2$, chlorine.

It has been experienced in operations that handle (or contain) acid-gas containing solutions such as amine units that corrosion problems are highly localized as in a certain section of an equipment of a pipe section within the unit, and overall corrosion is not encountered. The localized corrosion is due to acid gases, and more specifically the release of acid gases ("acid gas flashing") which comes into contact with mild steel causing equipment failure. The invention relates to an improved method and a system (herein after "system" or "corrosion assessment system") to predict corrosion in operations handling acid-gas containing solutions such as an amine unit. The embodiments takes into account acid gas flashing as a factor in causing localized corrosion. In one embodiment, the system takes into account the operating limits of the unit to optimize the operation and maximize the acid gas treating rate, taking into account the localized corrosion risk within the unit.

Figure 1:
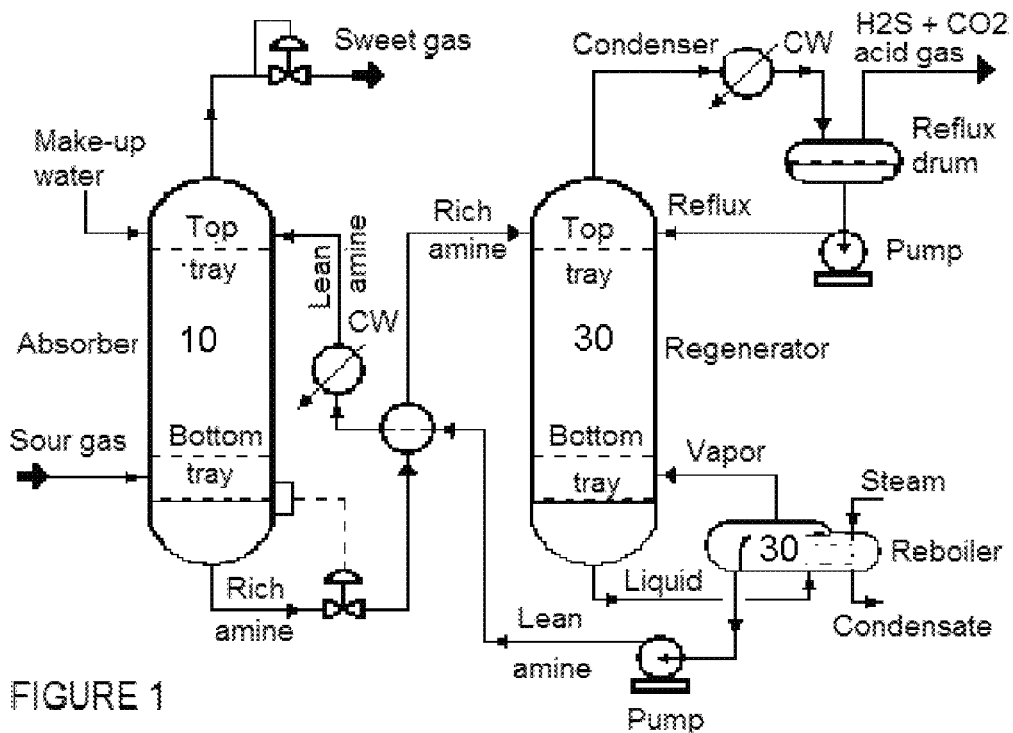
FIG. 1 is a diagram illustrating an embodiment of an amine unit.

Amine Unit Operation & Corrosion:

In operations that handle acid-gas containing solutions such as an amine unit, equipment (including the piping network) typically experiences a loss of material in the wall thickness when it is corroded, leading to a weakening of the equipment and eventually failure in the form of a leak. FIG. 1 gives a generalized overview of an exemplary operation such as an amine plant with various pieces of equipment and a piping system that can be subject to corrosion. As shown, (lean) amine solutions are used to remove hydrogen sulfide ($H_2S$) and mercaptans from process streams in absorber 10 generating a rich amine stream. The process streams can be a gas stream ("sour gas" as shown) or a light hydrocarbon liquid stream. Carbon dioxide ($CO_2$) and many other acid species are also absorbed by the amine solution from the process streams. The rich amine solution undergoes stream stripping in stripper 20 for the removal of weak acids such as $H_2S$ and $CO_2$, wherein the stripping steam is generated in a reboiler 30 that takes its feed from the regenerator tower below the steam stripping section. Condensing water from the effluent water/acid gas stream from the top of the regenerator helps minimize water usage. The stream stripping is not complete so residual $H_2S$ and $CO_2$ remain in the lean amine solution. Many of the acids that are not removed by steam stripping are called Heat Stable Salts (HSS) or, unless otherwise neutralized, Heat Stable Amine Salts (HSAS). Examples include but are not limited to formate, acetate, glycolate, propionate, oxalate, chloride, sulfate, thiosulfate, and thiocyanate.

Figure 2:
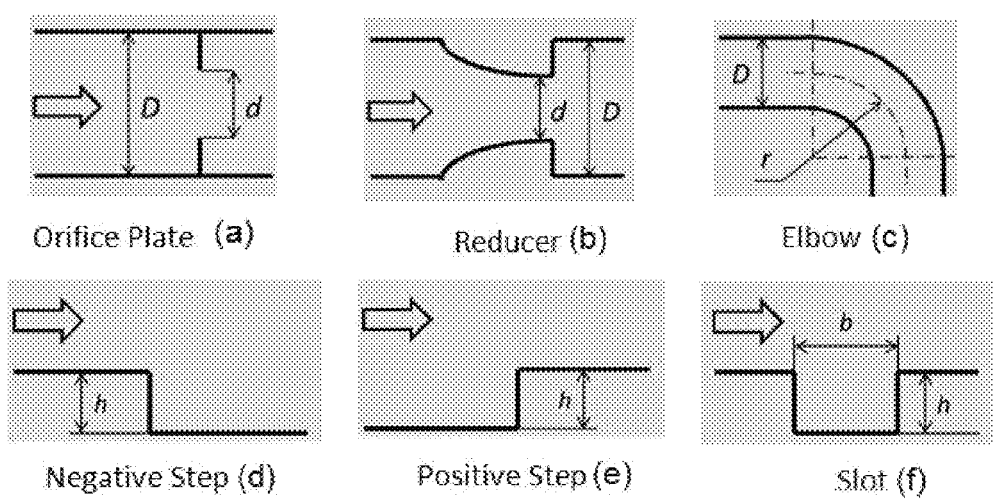
FIG. 2 shows exemplary components in equipment and/or a piping network in an amine unit that can be subject to localized corrosion.

In addition to the piping network and equipment as shown in FIG. 1, there are other equipment pieces not shown in the Figure that can be subject to corrosion in an amine unit such as storage tanks, charge pumps, heat exchangers, filters, flash drums, coalescers, feed drums, connecting pipes, etc. FIG. 2 illustrates various locations in the piping network and equipment in an amine units that are susceptible to localized corrosion, including but not limited to reducer, elbow, orifice plate, negative step, positive step, and slot. These locations are representative of entrance conditions that a fluid experiences when flowing from one section of equipment to another (e.g., an elbow), or from a pipe into or out of a piece of equipment (e.g., flowing from the tube sheet end of a heat exchanger, or flowing out of an equipment). Corrosion in the bottom of the absorber, on the rich side of the heatexchanger, hot rich piping, pressure let down valve or top of the regenerator, and connecting piping around these areas is generally considered rich amine corrosion.

In the amine units, when there is a change in the equilibrium between the acid gases, e.g., $H_2S$, $CO_2$, $SO_2$, $NO_2$ and combinations, etc., in a solute such as amine or water, the acid gases are liberated resulting in corrosion when the acid gases come into contact with mild steel. The liberation of acid gases can be caused by changes in operating parameters, e.g., temperature increase and pressure reduction. The method and system provided herein provide for corrosion assessment taking into account the hydraulic effects which can cause the equilibrium in a unit that handles acid-gas containing solution(s) such as amine units to shift sufficiently allowing acid gas to escape from solution, e.g., acid gas flashing.

Corrosion Evaluation System:

The system that employs the model for corrosion assessment in one embodiment comprises software and/or firmware (e.g., executable instructions) encoded on a tangible (e.g., non-transitory) computer readable medium such as memory or a storage device medium (e.g., CD, DVD, among others) and executed by a computer processor. In one embodiment, the system contains components including but not limited to a processor, memory, network interface, peripheral I/O interface. The network interface enables communications over a local area network (LAN), a wide area network (WAN), over a radio frequency (RF) and/or optical fiber network and the like. In one embodiment, the system interfaces with controllers, instruments, sensors, etc. in the amine unit, for automatic input of parameters such as rates, temperature, pressure, etc.

In some embodiment, functionality associated with one or more of the various components of the corrosion assessment system may be implemented in hardware logic, e.g., a programmable logic device (PLD), a programmable gate array (PGA), a field programmable gate array (FPGA), an application-specific integrated circuit (ASIC), a system on chip (SoC), and a system in package (SiP). In other embodiments, the system may be implemented as a combination of hardware logic and processor-executable instructions (software and/or firmware logic). In yet other embodiments, one or more components of the corrosion assessment system may be distributed among several devices, co-located or located remote from each other.

The peripheral I/O interface provides for input and output signals, for example, user inputs from a mouse or a keyboard (e.g., to enter data into a graphical user interface), and outputs for connections to a printer or a display device (e.g., computer monitor). The software (e.g., software logic or simply logic) may include graphical user interface (GUI) logic as well as computation logic. In one embodiment, the computation logic comprises executable code embedded with one or more algorithms to perform computations and predictions on corrosion rate, fluid velocity, shear stress, etc. Further description of the various functionality of the computation logic is described below in association with the different output graphics, which provides for the display of a GUI that enables the receipt of user information, and/or generates output graphics (or simply, graphics or visualizations) providing an assessment of the corrosion risk to the amine unit. In one embodiment, the system contains software model that is EXCEL-based.

Figures 3A, 3B:
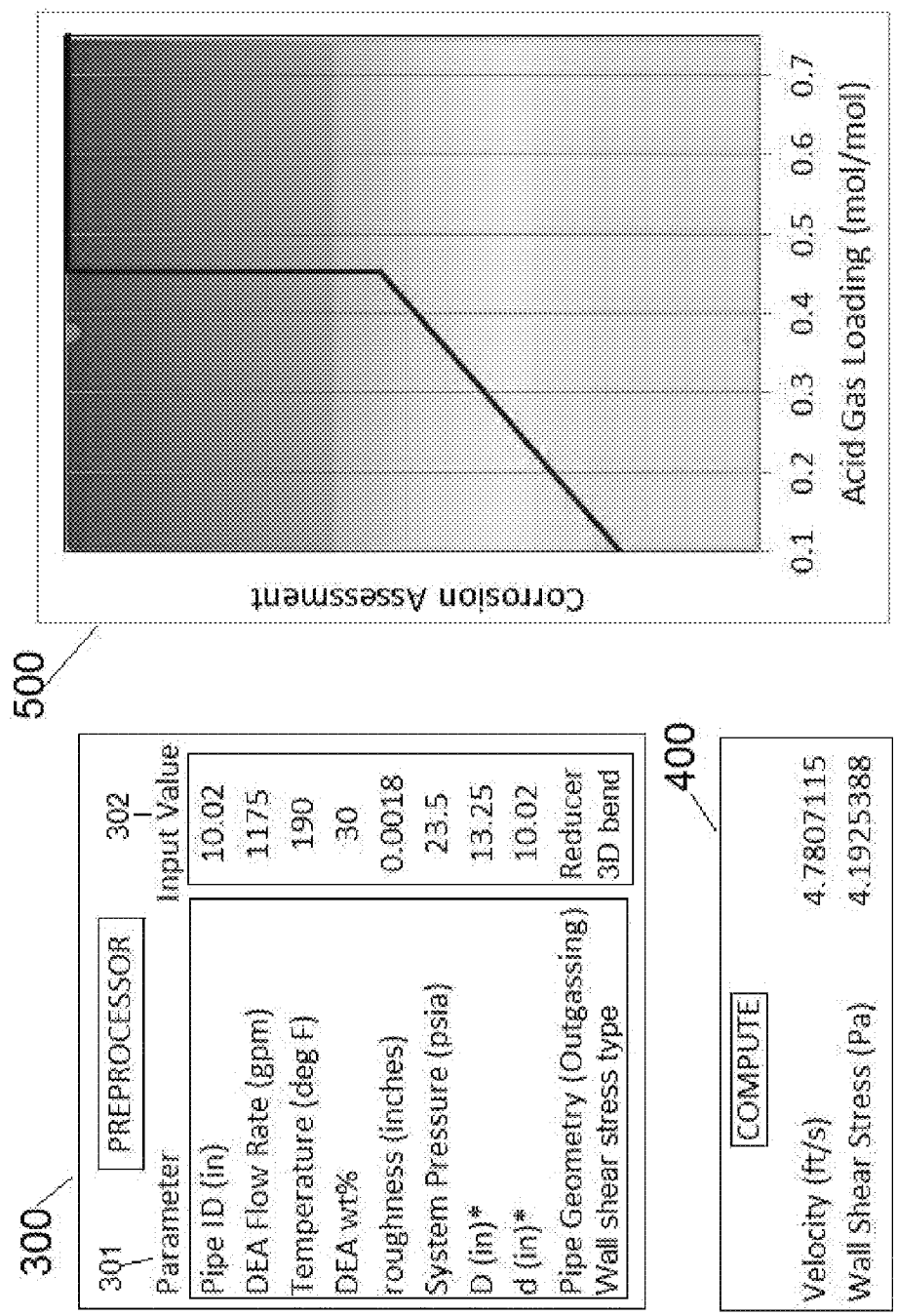
FIG. 3A is a screen diagram of an embodiment of an example graphical user interface (GUI) for the input of various parameters enabling the estimates of various parameters for the corrosion assessment, and the output of representative calculations.
FIG. 3B is a screen diagram that illustrates an example of a graphic output illustrating corrosion risk assessment as a function of acid gas loading.

FIG. 3A is a screen diagram showing an embodiment of an example graphical user interface (GUI) 300 that enables the input of various parameters into a system for corrosion assessment in a unit that handles acid-gas containing flowing solute(s), and an example output graphic 400 showing some of the values as computed by the system. The example GUI 300 comprises an input description section 301 and a corresponding data entry section 302. Some or all of the values can be entered by the user, or selected from a drop down menu, e.g., slot, orifice plate, elbow, etc., for the pipe geometry; straight, 90 degree elbow, 3D bend, weld protrusion of a certain size, etc., for wall shear stress type. Although not shown, in one embodiment the GUI includes other input values including but not limited to amine type (e.g., DEA, MEA, etc.), $CO_2$ concentration, $CO_2/H_2S$ ratio, metallurgical factors (e.g., alloy composition/type, microstructure of the surface, etc.); and hydrodynamic factors (e.g., flow regime such as slog flow, stratified flow, etc.). In one embodiment, the output graphic 400 also includes other values computed by the system including but not limited to local pressure drop, etc.

FIG. 3B is a screen diagram illustrating an example output graphic 500 as provided by an embodiment of the corrosion assessment system. In one embodiment as shown, the output graphic 500 illustrates the overall corrosion risk to the unit. In another embodiment, the output illustrates the corrosion evaluation to an equipment in the unit, or to a particular section of the piping network in the unit. The corrosion risk assessment can be quantitative in terms of corrosion rate, e.g., mpy (mils per year), or it can be qualitative in terms of operation zones, e.g., a green zone for a safe operating zone in terms of acid gas loading to the unit; a yellow zone for cautious operations, wherein the acid gas loading is approaching level close to acid gas flashing causing corrosion to the equipment; and a red zone for where acid gas flashing occurs and corrosion is expected. The acid gas loading in one embodiment is expressed as mole of $H_2S$ per mole of amine, as MEA, DEA, etc. or mixtures thereof. The higher the acid gas loading, the higher the capability of the amine unit and correspondingly, the higher refinery capability as $H_2S$ removal rate goes up with amount of processed crude.

Corrosion Assessment Method:

It is observed that when flashing of an acid gas such as $H_2S$, $CO_2$, $SO_2$, $NO_x$, $SO_x$, etc. occurs, corrosion is very aggressive even at low velocities. It is also observed that local pressure drops can be many times higher than the system pressure drop. The embodiments take into account the parameters associated with the specific sections in the unit to determine if and when the increased velocity of entrance, causes the velocity pressure to increase and the localized pressure to decrease with break out of acid gases. The embodiments take into account a key factor not considered in the prior art, acid gas flashing as a function of system pressure and local temporary pressure drop ("localized pressure drop" such as vena contracta). Flashing occurring in localized sections of the unit due to any of dissolved acids such as $H_2S$, $CO_2$, or hydrocarbons (e.g., $CH_4$) can be permanent or temporary (cavitation).

The embodiments can be used for the corrosion assessment of units handling acid-gas containing solute(s), determining the maximum loading at which a system operates above the minimum pressure to keep all of the solution in the liquid phase, given the equipment parameters and operating conditions. In one embodiment, the operation of the corrosion assessment system begins with the calculation of the pressure drop for the specific equipment being considered, e.g., a reducer, an elbow, etc. The calculations are based on empirical correlations based on the selected geometry parameters and process conditions. The pressure drop calculation, e.g., the minimum pressure in the system, is calculated by subtracting the previously calculated pressure drop from the total system pressure as input to the system.

Figure 4:
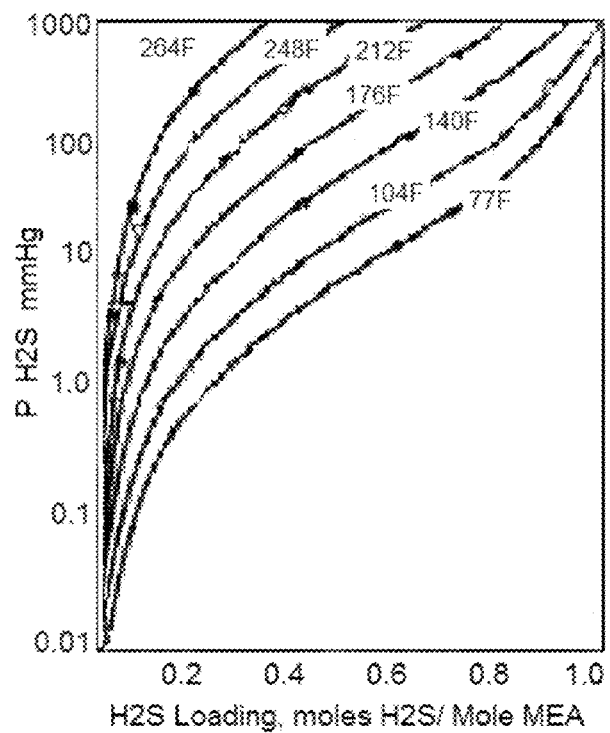
FIG. 4 is an exemplary plot showing $H_2S$ partial pressure as a function of $H_2S$ loading at different temperatures.

In one embodiment, thermodynamics modeling is carried out within the system by a thermodynamics module, e.g., a commercially available physical property analysis software, to determine one or more thermodynamic values and equilibrium constant based on the input parameter values. In another embodiment, the system comprises a database, stored in memory, containing pre-determined calculations representing thermodynamic values as a plurality of vapor and saturation pressure curves at different temperatures for different acid gas loadings (as concentrations of acid gas in the solute, e.g., mole of $H_2S$ per mole amine, or concentration or wt. % of ammonium bisulfide in solution, etc.) as illustrated in FIG. 4. The maximum acid gas loading at the system temperature for the calculated minimum pressure can be determined from the thermodynamics module, or from the predetermined values in the database (e.g., vapor and saturation pressure curves).

Figure 5:
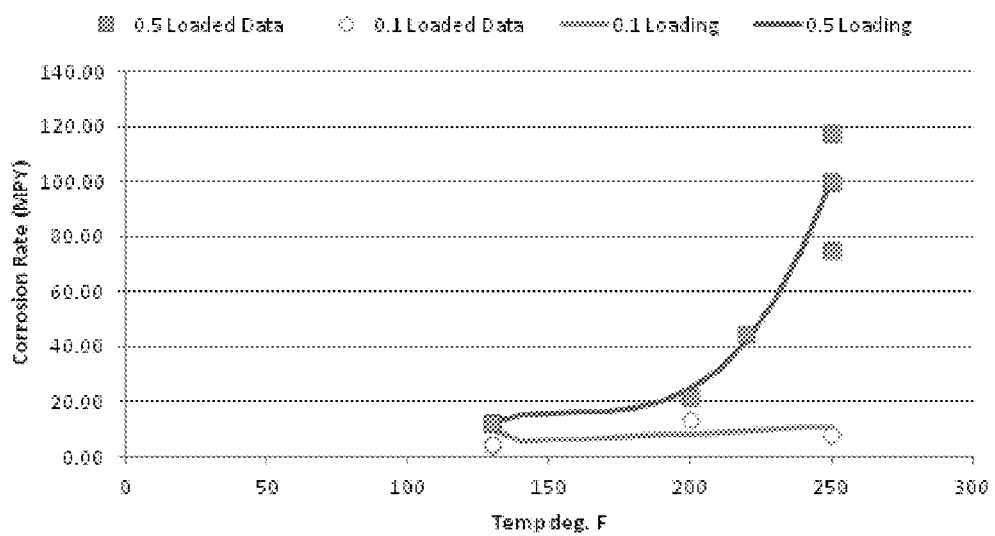
FIG. 5 is an exemplary plot showing the corrosion rate as a function of temperature at different $H_2S$ loadings and under flowing conditions.

The embodiments further comprise corrosion rate data for the predicted maximum acid gas loading as well as other gas loading. In one embodiment, the corrosion rate evaluation is carried out within the system using corrosion models known in the art, including but not limited to mechanistic and empirical models known in the art, e.g., models by C. de-Waard, Neborg, Kermani, and Nesic. In another embodiment as illustrated in FIG. 5, the system comprises a database containing pre-determined calculations representing corrosion rates at different gas loadings (e.g., mole $H_2S$ per mole amine) and at different temperatures. Corrosion rate for individual sections within the amine unit under different operating conditions, e.g., operating concentrations or acid gas loading (e.g., mole $H_2S$ per mole amine) up to the maximum acid gas loading can be determined from the corrosion model or the predetermined values in the database.

Figure 6:
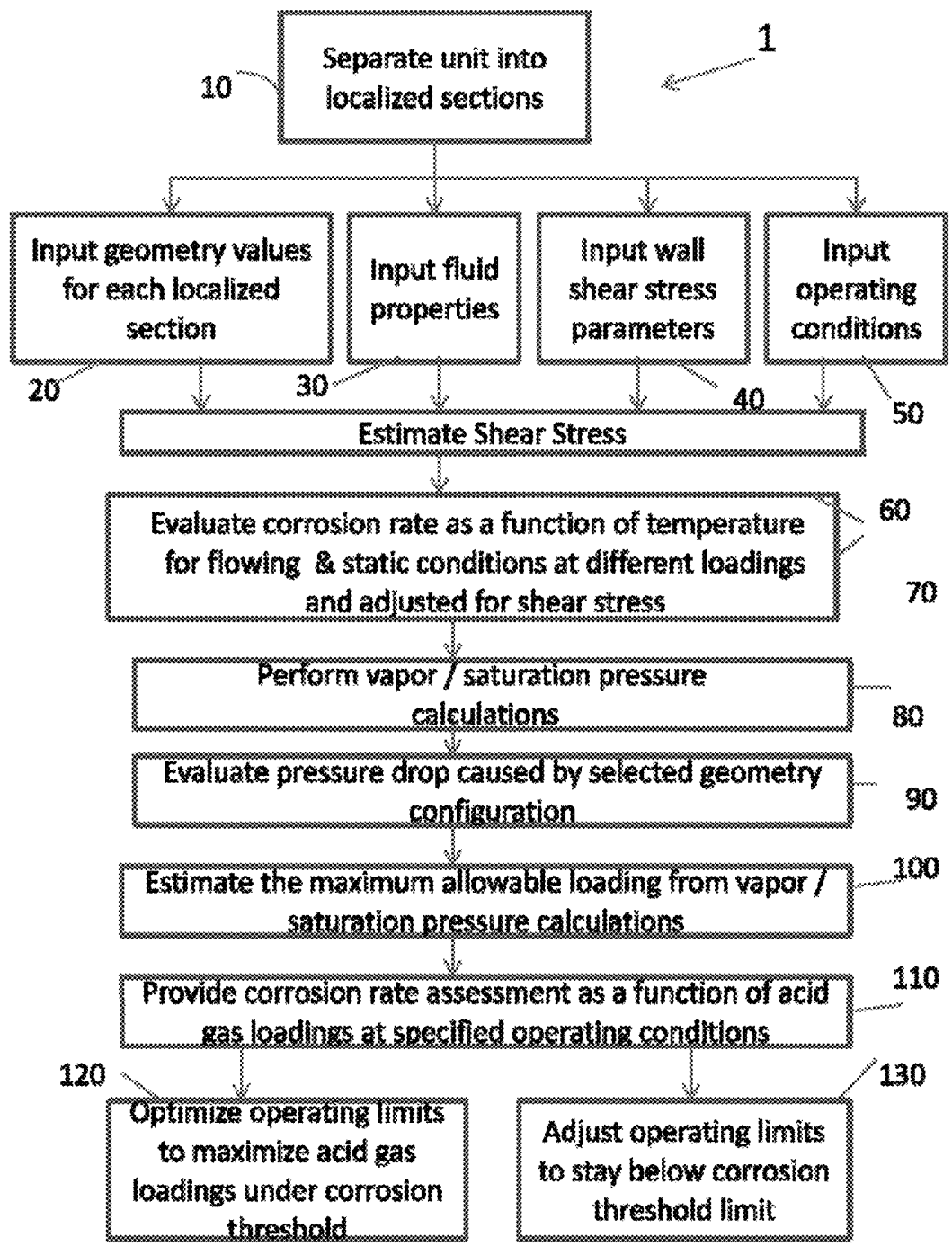
FIG. 6 is a flow chart of a method and implemented by a system, e.g., a process to optimize the performance of an amine unit to maximize gas treating rate while keeping corrosion under control.

FIG. 6 is a flow chart of one embodiment of a corrosion assessment method. It should be noted that the steps are not necessarily performed serially in the sequence as shown, as some of the steps can be performed concurrently (e.g., obtaining input data from an operator and/or automatic sensors at the same time, or calculations of corrosion rates can be done simultaneously with thermodynamics modeling), or not necessarily in the order as shown (e.g., thermodynamic calculations can be done before, after, or concurrently with corrosion modeling). Additionally, instead of calculations based on empirical models, thermodynamics and/or corrosion rate data can simply be retrieved from database(s).

In step 10, the unit may be simplified into certain equipment, or sections, or parts, for localized corrosion risk assessment, e.g., valves, weld protrusions, reducers, elbows, exchanger tubes, inlet/outlet nozzles, etc. Multiple sections within an equipment can be evaluated at the same time for corrosion risk to determine the equipment's maximum capacity before corrosion failure is to be expected. In step 20, an operator may determine a value or a range of values for multiple parameters associated with the particular equipment or part of the network for data entry. For example, the operator may enter geometry parameters associated with a part susceptible to localized corrosion, e.g., valves, inlet/outlet nozzles, exchanger tubes, reducers, slots, etc. Depending on the shape of the components, input geometry parameters include but are not limited to the shape of the components, the width and height for a slot opening, the arc length, length of a pipe, the degree/curvature of a bend ("r"), inside diameter D, inlet radius and outlet radius for a reducer, orifice plate opening d, height h of a slot, the width of a slot, etc.

In step 30, an operator may enter fluid properties such as the solute composition, e.g., amine type, lean amine loading/rich amine loading (e.g., amine concentration such as 15% MEA, 30% MDEA, etc.), acid gas content (e.g., $H_2S$, $CO_2$, $NO_x$, other hydrocarbons, etc.) content, heat stable salts (HSS) contents, etc.; the number of phases (liquid, gas, etc.); density, viscosity, etc, or the data (some or all) can be automatically obtained from on-line sensors/analyzers. The solute type can be a mixture of amines, e.g., DEA, MDEA, DIPA, proprietary amines, and mixtures thereof, etc. In step 40, the operator may also determine and input parameters for shear stress calculations such as surface roughness on a pipe section, weld protrusions, etc. Step 50 relates to the input of operating parameters such as system pressure, temperature, etc., which can be entered by an operator or obtained automatically through on-line sensors connected to the system.

In one embodiment starting in step 60, shear stress calculations are carried out. The correlations may take the form of fluid dynamic modeling using known friction factor equations such as Zigrang & Sylvester, or developed at least in part by using empirically derived data. In certain embodiments, shear stress calculation at the pipe wall is computed taking into account, turbulence and velocity of the fluids in the system. In other embodiments, a shear stress value is calculated taking into account the selected geometry and associated parameters of the equipment in the amine unit to be evaluated.

Figure 7:
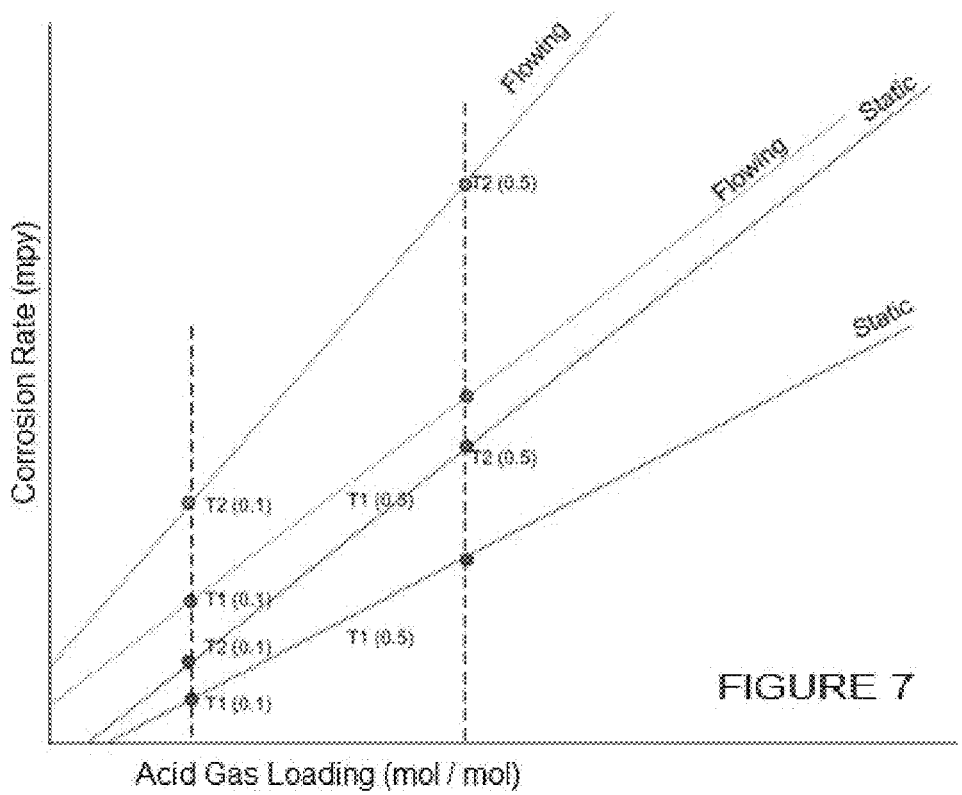
FIG. 7 is another exemplary plot showing the loading interpolation lines for different temperature conditions for different conditions.
Figure 8:
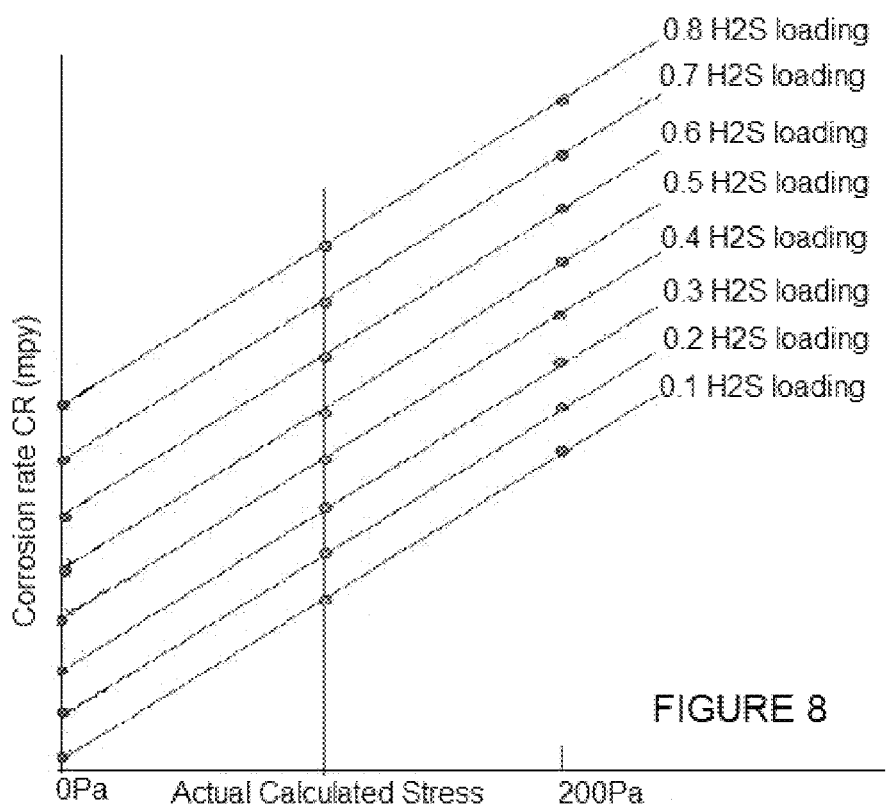
FIG. 8 is an exemplary plot showing shear stress interpolation lines for different acid gas loadings.

Step 70 in one embodiments comprises the development of corrosion rate data in the particular acid-gas containing solute system, e.g., rich amine solvents at different $H_2S$ loadings as a function of temperature, corrosion rates experienced in sulfur dioxide or sulfur trioxide containing system, etc. In one embodiment, corrosion data is interpolated or extrapolated from a database containing quantitative corrosion data developed from simulated lab tests and/or actual experience in amine units, with corrosion rate measurements in different materials, e.g., carbon steel, stainless steel 304 SS, 316 SS, alloy steel, etc., under different scenarios/variables such as varying acid gas concentrations, velocities, temperatures, heat stable salts, and amine concentrations, etc. In another embodiment, corrosion data is developed from mechanistic and/or empirical models. The empirical models are developed from a database of quantitative corrosion data. The corrosion rate data can be established for flowing conditions as well as for static conditions as illustrated in FIG. 7. For example, the corrosion rate (in mpy) in one embodiment for a $H_2S$ loading of 0.5 mole/mole DEA (30 wt. %) in flowing conditions can be expressed as: $y=0.0001T^3-0.0532T^2+8.5279T-440.2126$, and $y=0.0495x-1.4159$ for a $H_2S$ loading of 0.1. The corrosion rate under static conditions is more linear and can be expressed as $y=0.1219x-15.479$ and $y=0.0358x-4.1583$ for $H_2S$ loading of 0.5 and 0.1 mole/mole DEA respectively. As illustrated in FIG. 8, the corrosion rate values are next adjusted (e.g., by interpolation) taking into account the correlated shear stress from step 60, as wall shear stress is expected to increase the corrosion rate with localized attack.

In step 80, thermodynamics of acid gases in the solute system is simulated. In one embodiment this step, the equilibrium partial pressure of an acid gas such as $H_2S$ (and optionally with other gases including hydrocarbons and $CO_2$) in aqueous amine systems is calculated to determine the minimum pressure to keep all of the solution in the liquid phase as a function of the specific composition and temperature. FIG. 5 illustrates representative correlations for $H_2S$ partial vapor pressure over an MEA solution of 15.3% at different temperatures.

The thermodynamics calculations can be based on various empirical and mechanistic models known in the art, such as the Kent and Eisenberg model or variations thereof as disclosed in "Prediction of $H_2S$ and $CO_2$ Solubilities in Aqueous Triethanolamine Solutions Using a Simple Model of Kent-Eisenberg Type" by Patil et al., Industrial & Engineering Chemistry Research, 2012, 51, pp. 6591-6597; or "Improved Kent-Eisenberg model for predicting $CO_2$ solubilities in aqueous diethanolamine (DEA) solutions," by Chakma et al., Gas Separation and Purification, 1990, Vol. 1, Issue 1, pp. 37-40, the disclosures are incorporated herein by reference in its entirety. In another embodiment, a commercially available physical property analysis software such as the Stream Analyzer model from OLI Systems, Inc., is employed. The OLI Stream Analyzer model is described in "A speciation-based model for mixed solvent electrolyte systems," Fluid Phase Equilibria 203 (2002) 141-176, the disclosure is incorporated herein by reference.

In step 90, adjustments are made to take into account the hydraulic effects that can cause an upset in the equilibrium between the acid gases and the amines. The upset causes the liberation of the acid gases, increasing the corrosion risk. It is known that the total pressure on a dynamic system such as the operation in an amine unit can be represented by a simplified equation as: $P_t = P_s + P_v$, with $P_t$ as the total system pressure, $P_s$ as the static pressure, and $P_v$ as the velocity pressure. The total pressure on a solute such as an amine solution at any one point is constant. If the velocity pressure increases, the static pressure must decrease. If there is a change in the static pressure (as in a localized pressure), the equilibrium of the liquid (such as amine) acid gas system can be upset. Temporary pressure drops causing a change in the static pressure are localized and related to changes in the geometry of the equipment (or locations within an equipment), fittings, valves, weld protrusions, etc., and cannot be captured by instrumentation.

As indicated, outgassing may happen if pressure is lower than the saturation pressure $P_{sat}$ of dissolved gases in a given aqueous solution, with $P_{sat}$ being defined by Henry's law: $P_{sat} = k_H c_g$, wherein $k_H$ is the Henry's law coefficient that is determined by the composition of both gas and solution, and depends upon the temperature T; $c_g$ is the gas concentration. The sum of the vapor pressure and the saturation pressure is the minimum pressure $p_m$ to prevent the release of gas from the solution, defining the borderline parameters for safe operations before significant corrosion risk due to released gas. The sum can be evaluated by the thermodynamic equilibrium in the solution as carried out in step 80. However, hydraulic elements in the unit as well as any obstacles or surface discontinuities (with geometry and shear stress parameters as input in step 10) will disrupt the homogeneous structure of the flow and create zones of locally low pressure.

In one embodiment of step 90, CFD simulations of the flow structure is carried out to account for the necessary adjustments due to the hydraulic effects. The simulations can be based on empirical data or models known in the art to evaluate the localized pressure drop due to the geometrical parameters. An example is presented in "Cavitation in An Orifice Flow" by Dabiri et al., Phys. Fluids, 2007, v. 19, article 072112, incorporated herein by reference in its entirety. The simulations can be carried out on an ad-hoc basis to evaluate the corrosion risk of a particular location in the unit, or pre-calculated for the various equipment in the unit, As localized pressure drop can result in flashing of dissolved gases and/or acid gas (e.g., $H_2S$), causing a break-out and significantly increased corrosion risk, the operating rate at which the highest corrosion risk occurs is identified in step 100 (e.g., the vertical line in FIG. 3B). This is the acid gas loading at which outgassing occurs, when the localized pressure drops below the sum of the vapor pressure and the saturation pressure of the dissolved gas.

The next step 110 evaluates the corrosion risk under different operating conditions taking into account the corrosion rate values in step 70 for the system temperature at different acid gas loadings after adjustment for shear stress. Corrosion rates are expected to increase with increasing acid gas loading. However, there is a significant corrosion risk when there is an acid gas break out with expected short-term failure of equipment, and this is the loading rate where outgassing occurs (causing a jump in the corrosion rate to indefinite as in FIG. 3B).

Applications:

Corrosion from acid gas flashing in operations handling acid containing solution(s) such as amine units is highly localized, aggressive, and difficult to detect by inspection. In one embodiment, the disclosed method and system herein can be used to identify sensitive locations or range of locations within the unit that are susceptible to high corrosion risk at high acid gas loading. The output can be a display of the unit wherein locations with a high probability of outgassing, or approaching the outgassing point are displayed on an interactive map. The locations can be targeted for the placement of corrosion monitoring instruments where they can help predict and/or prevent equipment failure. For amine units, examples include rich amine piping from absorbers, particularly around valves and if downstream pressure are low. The embodiments can also be employed to identify acid gas break-out locations in regenerator system as amine is heated and pressures are low.

The embodiments can be employed on an ad-hoc basis, intermittently, or continuously as a part of a facility's monitoring system. They can be used to optimize operations of a unit. Knowing the corrosion risks for the different sensitive areas in the unit, the plant can determine the optimal loading to the amine unit and adjust operating parameters, e.g., flow rate, amine type/concentrations, temperature, pressure, etc., if necessary to keep the corrosion risk under control as the operation approaches the high corrosion risk zone. The adjustment of operating parameters in one embodiment comprises chemical treatment, e.g., addition of corrosion inhibitors, wherein the system automatically instructs control equipment configured for the addition of treatment fluids to the unit or the piping system, or automatically adjusting one of the operating parameters to prevent the acid gas flashing from happening.

The corrosion evaluation systems and methods can also be used in conjunction with known optimization methods in the art, e.g., improving efficiency of the unit by using selective/proprietary amines, increasing amine concentrations, varying amine mixtures (e.g., DEA vs. DEA and MDEA mixture, etc), varying $H_2S/C_{O2}$ mixtures, varying lean amine temperatures, etc. A simulation of the maximum operating rates of the different equipment in the amine unit in advance allows the unit efficiency to be optimized with minimal risk of equipment failure due to corrosion caused by acid gas flashing.

The systems and methods can also be used to define optimal operations of an amine unit. Operations at different acid gas loadings can be simulated either individually for different sections within an equipment, or an integrated basis for different pieces of equipment, to identify equipment or sections within the piping network that would limit the operation of the unit and reach the high corrosion risk level before other equipment in the unit. The locations can also be targeted for the selective replacement for equipment that is less likely to be susceptible to corrosion risks by design, or with more corrosion tolerant material of construction, allowing the amine unit to operate at optimal rates.

In one embodiment, the system is employed to continuously evaluate the corrosion risk in multiple equipment (or sections) within a unit in conjunction with monitoring the acid gas loading to the unit, sending out warnings to operators if the operation is approaching a point where there is a high corrosion risk to one or more equipment pieces in the unit. For example, an alarm point can be set when the operation is within a certain percentage, e.g., 10%, 5%, 2%, etc. of the lowest maximum acid gas loading for a critical piece of equipment in the amine unit. The embodiments can be used in conjunction with other modeling and optimization methods/systems, for the automatic adjustment of other units with controllers, e.g., temperature control, adjustment of amine mixtures, etc. when the operation approaches the critical limit when acid gas flashing is expected to prevent such happenings.

The embodiments can also be used to map a safe (i.e., low corrosion risk) operating zone for a unit, with advance simulations of different equipment (and/or locations) within the unit as to define parameters at which outgassing causing acid gas flashing is thermodynamically impossible. The safe operating maps can be defined by: a) hydraulic elements or features that disrupts a flow; b) major geometrical dimensions of the piping elements within allowing for a safe operation; c) temperature of the liquid in the flow; d) chemical composition of the liquid assumed to be an aqueous solution; and e) concentration of the dissolved gases. Factors c) and d) define the gas solubility coefficient that contributes to the definition of the minimum pressure preventing gas release from the solution under static conditions.

The disclosed embodiments can also be used in conjunction with a database system, keeping track of the frequency and duration, and which equipment pieces have been exposed to high corrosion with incidents of high acid gas loading (e.g., where acid gas loading exceeds the rate indicated by the vertical line in FIG. 3B). The database can be part of an overall maintenance plan to selectively replace or maintain equipment indicated by the system to have been frequently exposed to high corrosion risk.

While some of the embodiments presented herein refer to the flashing (or outgassing) of $H_2S$ from amine solutions, it is not simply limited to this phenomena. As discussed, the embodiments can be applied to the release of gasses leading to localized corrosion in other streams both within a refinery or a petrochemical plant, as well as in other units and operations in other industries. Examples include but are not limited to corrosion risk evaluation of releases of corrosive gases from sour water, outgassing of corrosive components from hydrocarbon streams, and analogous processes in alkylation, steam generation, and other units where potentially corrosive gases are dissolved in a flowing solute.

To the extent that systems and methods are described in object-oriented terms, there is no requirement that the systems and methods be implemented in an object-oriented language. Rather, the systems and methods can be implemented in any programming language, and executed on any hardware platform. Any software components referred to herein include executable code that is packaged, for example, as a standalone executable file, a library, a shared library, a loadable module, a driver, or an assembly, as well as interpreted code that is packaged, for example, as a class. The flow diagrams herein provide examples of the operation of the corrosion evaluation systems and methods. Blocks in these diagrams represent procedures, functions, modules, or portions of code which include one or more executable instructions for implementing logical functions or steps in the process. Alternate implementations are also included within the scope of the disclosure. In these alternate implementations, functions may be executed out of order from that shown or discussed, including substantially concurrently or in reverse order, depending on the functionality involved.

The foregoing description of illustrated embodiments of the present disclosure, including what is described in the abstract, is not intended to be exhaustive or to limit the disclosure to the precise forms disclosed herein. While specific embodiments of, and examples for, the disclosure are described herein for illustrative purposes only, various equivalent modifications are possible within the spirit and scope of the present disclosure, as those skilled in the relevant art will recognize and appreciate. As indicated, these modifications may be made to the present disclosure in light of the foregoing description of illustrated embodiments.

Thus, while the present disclosure has been described herein with reference to particular embodiments thereof, a latitude of modification, various changes and substitutions are intended in the foregoing disclosures, and it will be appreciated that in some instances some features of embodiments of the disclosure will be employed without a corresponding use of other features without departing from the scope of the disclosure. Therefore, many modifications may be made to adapt a particular situation or material to the essential scope of the present disclosure. It is intended that the disclosure not be limited to the particular terms used in following claims and/or to the particular embodiment disclosed as the best mode contemplated for carrying out this disclosure, but that the disclosure will include any and all embodiments and equivalents falling within the scope of the appended claims.

The invention claimed is:

1. A method for evaluating corrosion risk in a unit handling an acid gas-containing solute, comprising:
   identifying at least a location in the unit for conducting the corrosion risk evaluation;
   receiving information about geometrical parameters of the location;
   receiving information about operating parameters, fluid dynamic properties, and properties of the solute in the unit;
   correlating fluid dynamics of the location in the unit with a shear stress value;
   predicting a corrosion rate for different acid gas loadings expressed as concentration of the acid gas in the solute responsive to the correlated shear stress;
   evaluating a localized pressure drop in the location due to the geometrical parameters;

correlating a relationship between vapor saturation pressure and temperature data for the different acid gas loadings;
identifying from the correlated vapor saturation pressure and temperature data a minimum pressure above which acid gas flashing from the solute occurs given the localized pressure drop, causing corrosion in the identified location.

2. The method of claim 1, further comprising:
displaying the predicted corrosion rate as a function of the different acid gas loadings as a visual display.

3. The method of claim 1, wherein the acid gas is $H_2S$, the solute is amine, and the acid gas loadings are expressed as moles of $H_2S$ per mole of amine.

4. The method of claim 1, further comprising
correlating the minimum pressure below which acid gas flashing of acid gas occurs with a maximum acid gas loading for the identified location.

5. The method of claim 4, further comprising:
adjusting the acid gas loading to the unit to keep the acid gas loading below the maximum acid gas loading for the identified location.

6. The method of claim 1, wherein the relationship between vapor saturation pressure and temperature data for the different acid gas loadings is correlated using a physical property software.

7. The method of claim 1, wherein the relationship between vapor saturation pressure and temperature data for the different acid gas loadings is correlated using an empirical model.

8. The method of claim 1, wherein the location is selected from any of a reducer, an elbow, an orifice plate, a negative step, a positive step, a slot, a pressure let down valve, and bottom of an absorber.

9. The method of claim 1, wherein the location is a tube sheet end of a heat exchanger.

10. The method of claim 1, wherein predicting a corrosion rate for different acid gas loadings responsive to the correlated shear stress comprises:
calculating corrosion rate for different concentrations of acid gas in the solute as acid gas loadings under static conditions using at least an empirical correlation;
calculating corrosion rate for different concentrations of acid gas in the solute as acid gas loadings under flowing conditions using at least an empirical correlation; and
interpolating the calculated corrosion rate taking into account the correlated shear stress to obtain a corrosion rate for different concentrations of acid gas in the solute as acid gas loadings.

11. The method of claim 1, wherein predicting a predicted corrosion rate for different acid gas loadings responsive to the correlated shear stress comprises:
providing a database containing corrosion rate data for different concentrations of acid gas in the solute under different static and flowing conditions;
obtaining from the database a predicted corrosion rate for different concentrations of acid gas in the solute as acid gas loadings; and
interpolating the predicted corrosion rate for different concentrations of acid gas in the solute as acid gas loadings taking into account the correlated shear stress.

12. The method of claim 1, wherein the corrosion risk evaluation is conducted for a plurality of locations in the unit to identify a maximum gas loading rate for each of the plurality locations.

13. The method of claim 12, where the location having a lowest maximum gas loading rate is identified for corrosion risk monitoring.

14. The method of claim 1, further comprising carrying out the corrosion risk evaluation for the at least a location under at least one of: varying solute types; varying acid gas concentrations in the solute; varying concentrations of the solute; varying temperatures; and combinations thereof.

15. The method of claim 1, wherein receiving information about operating parameters, fluid dynamic properties, and properties of the solute in the unit comprises
obtaining at least one of operating parameters, fluid dynamic properties, and properties of the solute in the unit from an on-line sensor; and
obtaining at least one of operating parameters, fluid dynamic properties, and properties of the solute in the unit from data entry by an operator.

16. The method of claim 1, for evaluating corrosion risk in any of an amine unit, a Reactor Effluent Air Cooler (REAC), a steam generation unit, and an alkylation unit.

17. A method for evaluating corrosion risk in an amine unit for removing $H_2S$ acid gas, comprising:
identifying a plurality of locations in the amine unit to identify a maximum acid gas loading for each location;
receiving information about geometrical parameters of each location;
receiving information about operating parameters, fluid dynamic properties, and properties of amine in the amine unit;
correlating fluid dynamics of each location in the amine unit with a shear stress value;
predicting a corrosion rate for each location at different concentrations of $H_2S$ in amine as acid gas loadings expressed as concentration of $H_2S$ in amine responsive to the correlated shear stress for each location;
evaluating localized pressure drop in each location due to the geometrical parameters;
correlating a relationship between vapor saturation pressure and temperature data for the different acid gas loadings; and
identifying from the correlated vapor saturation pressure and temperature data a maximum acid gas loading for each of the identified locations, given the localized pressure drop in each location, above which maximum loading rate flashing of $H_2S$ occurs.

18. The method of claim 17, further comprising:
identifying a location having the lowest maximum acid gas loading; and
monitoring the location having the lowest maximum acid gas loading for corrosion risk.

19. The method of claim 18, further comprising:
adjusting the acid gas loading to the amine unit to below the lowest identified maximum acid gas loading.

20. The method of claim 17, wherein the relationship between vapor saturation pressure and temperature data for different acid gas loadings is correlated using a physical property software.

21. The method of claim 17, wherein the location is selected from any of a reducer, an elbow, an orifice plate, a negative step, a positive step, a slot, a pressure let down valve, and bottom of an absorber.

22. The method of claim 17, wherein the location is a tube sheet end of a heat exchanger.

23. The method of claim 17, wherein the relationship between vapor saturation pressure and temperature data for different acid gas loadings is correlated using a physical property software.

24. The method of claim 17, wherein the relationship between vapor saturation pressure and temperature data for different acid gas loadings is correlated using an empirical model.

25. The method of claim 17, wherein predicting a corrosion rate for each location at different concentrations of $H_2S$ in amine as acid gas loadings responsive to the correlated shear stress for each location comprises:
  providing a database containing corrosion rate data for different concentrations of $H_2S$ in amine under different static and flowing conditions;
  obtaining from the database a corrosion rate for different concentrations of $H_2S$ in amine as acid gas loadings; and
  interpolating from the corrosion rate from the database a corrosion rate for different concentrations of $H_2S$ in amine as acid gas loadings taking into account the correlated shear stress.

26. The method of claim 17, wherein predicting a corrosion rate for each location at different concentrations of $H_2S$ in amine as acid gas loadings responsive to the correlated shear stress for each location comprises:
  calculating a corrosion rate at different concentrations of $H_2S$ in amine under static conditions using at least an empirical correlation;
  calculating a corrosion rate at different concentrations of $H_2S$ in amine under flowing conditions using at least an empirical correlation; and
  interpolating the calculated corrosion rate at different concentrations of $H_2S$ in amine as acid gas loadings taking into account the correlated shear stress.

27. The method of claim 17, further comprising carrying out the corrosion risk evaluation for the plurality of locations under at least one of: varying amine types; varying $H_2S$ and $CO_2$ concentrations; varying amine concentrations; varying temperatures; and combinations thereof.

28. The method of claim 17, wherein receiving information about operating parameters, fluid dynamic properties, and properties of amine in the amine unit comprises:
  obtaining at least one of operating parameters, fluid dynamic properties, and properties of amine in the amine unit from an on-line sensor; and
  obtaining at least one of operating parameters, fluid dynamic properties, and properties of amine in the amine unit from data entry by an operator.

29. A system for evaluating corrosion risk in a unit handling an acid gas containing solute, the system comprises a processor, wherein the processor is configured to
  receive information about geometrical parameters of a location within the unit;
  receive information about properties of the solute, fluid dynamic properties, and operating parameters in the unit;
  correlate fluid dynamics of the location in the unit with a shear stress value;
  predict a corrosion rate for different acid gas loadings expressed as concentration of the acid gas in the solute responsive to the correlated shear stress;
  evaluate a localized pressure drop in the location due to the geometrical parameters;
  correlate a relationship between vapor saturation pressure and temperature data for the different acid gas loadings;
  determine from the correlated vapor saturation pressure and temperature data a maximum acid gas loading, given the localized pressure drop in the location, above which maximum loading rate flashing of acid gas from the solute occurs.

30. The system of claim 29, further comprising at least a sensor for providing information about at least one of properties of the solute, fluid dynamic properties, and operating parameters in the unit.

31. The system of claim 29, wherein the processor is further configured to
  instruct a treatment equipment configured to add at least a corrosion inhibitor to the unit before flashing of acid gas occurs.

32. The system of claim 29, wherein the processor is further configured to
  instruct a controller equipment configured to adjust at least an operating parameter in the unit to prevent flashing of acid gas.

33. The system of claim 29, wherein the unit is selected from an amine unit, a Reactor Effluent Air Cooler (REAC), a steam generation unit, and an alkylation unit.

34. The system of claim 33, wherein the unit is an amine unit, the acid gas is $H_2S$, and the solute is amine.

35. A computerized prediction system for identifying locations within a unit handling acid gas containing solute susceptible to corrosion risk, comprising:
  one or more processing units for executing program instructions; and
  a program memory, coupled to one or more processing units, for storing a computer program including program instructions that when executed by the one or more processing units, is capable of causing the computer system to perform a number of operations comprising:
  receiving information about geometrical parameters of at least a location in the unit;
  receiving information about operating parameters, fluid dynamic properties, and properties of the solute in the unit;
  correlating fluid dynamics of the location in the unit with a shear stress value;
  predicting a corrosion rate for different acid gas loadings expressed as concentration of acid gas in the solute responsive to the correlated shear stress;
  evaluating a localized pressure drop in the location due to the geometrical parameters;
  correlating a relationship between vapor saturation pressure and temperature data for the different acid gas loadings; and
  identifying from the correlated vapor saturation pressure and temperature data a maximum acid gas loading, given the localized pressure drop in the location, above which maximum loading rate flashing of acid gas occurs causing corrosion in the location.

36. The system of claim 35, wherein predicting a corrosion rate for different acid gas loadings responsive to the correlated shear stress comprises:
  calculating a corrosion rate at different concentrations of acid gas in the solute under static conditions using at least an empirical correlation;
  calculating a corrosion rate at different concentrations of acid in the solute under flowing conditions using at least an empirical correlation; and
  interpolating the calculated corrosion rate at different concentrations of acid gas in the solute as acid gas loadings taking into account the correlated shear stress.

37. The system of claim 35, further comprising:
  an input peripheral, coupled to at least one of the processing units, for receiving information about at least one of operating parameters, fluid dynamic properties, and properties of the solute in the unit;

an output peripheral, coupled to at least one of the processing units, for presenting user-readable output showing the maximum acid gas loading, above which flashing of acid gas occurs causing corrosion in the location.

38. The system of claim 35, further comprising:
a memory resource, coupled to at least one of the processing units, for storing corrosion rate for different acid gas loadings under any of different operating parameters, fluid dynamic properties, and properties of the solute.

39. The system of claim 35, wherein predicting a corrosion rate for different acid gas loadings responsive to the correlated shear stress comprises:
obtaining from the memory source corrosion rate data for different concentrations of $H_2S$ in amine under different static and flowing conditions; and
interpolating the corrosion rate data from the memory source to obtain corrosion rate for different concentrations of $H_2S$ in amine as acid gas loadings taking into account the correlated shear stress.

40. A system for evaluating corrosion risk in an amine unit, wherein the processor is configured to
receive information about geometrical parameters of a location within the amine unit;
receive information about properties of the amine, fluid dynamic properties, and operating parameters in the amine unit;
correlate fluid dynamics of the location in the unit with a shear stress value;
predict a corrosion rate for different acid gas loadings expressed as concentration of $H_2S$ in amine responsive to the correlated shear stress;
evaluate a localized pressure drop in the location due to the geometrical parameters;
correlate a relationship between vapor saturation pressure and temperature data for the different acid gas loadings; and
determine from the correlated vapor saturation pressure and temperature data a maximum acid gas loading, given the localized pressure drop in the location, above which flashing of $H_2S$ from amine occurs.

41. The system of claim 40, wherein the processor is further configured to:
instruct a controller equipment in the amine unit configured to adjust at least an operating parameter in the unit to prevent flashing of $H_2S$.

42. The system of claim 40, wherein the processor is further configured to:
instruct at least a control device in the amine unit configured to adjust at least an operating parameter in the unit to prevent flashing of acid gas.

43. The system of claim 40, wherein the system further comprises:
at least a control device and wherein the control device adjust at least one of operating parameters in the amine unit in responsive to the maximum acid gas loading.

* * * * *